US012569213B2

(12) United States Patent
Horiuchi et al.

(10) Patent No.: US 12,569,213 B2
(45) Date of Patent: Mar. 10, 2026

(54) INFORMATION PROCESSING APPARATUS, INFORMATION PROCESSING METHOD, AND INFORMATION PROCESSING PROGRAM

(71) Applicant: FUJIFILM CORPORATION, Tokyo (JP)

(72) Inventors: Hisatsugu Horiuchi, Tokyo (JP); Masataka Sugahara, Tokyo (JP); Takeyasu Kobayashi, Tokyo (JP)

(73) Assignee: FUJIFILM CORPORATION, Tokyo (JP)

( * ) Notice: Subject to any disclaimer, the term of this patent is extended or adjusted under 35 U.S.C. 154(b) by 279 days.

(21) Appl. No.: 18/475,225

(22) Filed: Sep. 27, 2023

(65) Prior Publication Data

US 2024/0108300 A1    Apr. 4, 2024

(30) Foreign Application Priority Data

Sep. 30, 2022    (JP) ................................. 2022-158968

(51) Int. Cl.
| | |
|---|---|
| *A61B 6/00* | (2024.01) |
| *A61B 6/50* | (2024.01) |
| *G06T 7/521* | (2017.01) |
| *G06T 7/593* | (2017.01) |
| *G06T 7/70* | (2017.01) |

(52) U.S. Cl.
CPC .............. *A61B 6/54* (2013.01); *A61B 6/4476* (2013.01); *A61B 6/488* (2013.01); *A61B 6/505* (2013.01); *G06T 7/521* (2017.01); *G06T 7/593* (2017.01); *G06T 7/70* (2017.01); *G06T 2207/10028* (2013.01); *G06T 2207/30196* (2013.01)

(58) Field of Classification Search
CPC ........... A61B 6/04; A61B 6/08; A61B 6/4476; A61B 6/488; A61B 6/505; A61B 6/54; G06T 2207/10028; G06T 2207/30196; G06T 7/52; G06T 7/593; G06T 7/70
See application file for complete search history.

(56) References Cited

U.S. PATENT DOCUMENTS

| | | | | |
|---|---|---|---|---|
| 2014/0016743 A1* | 1/2014 | Egli | ....................... | G01B 15/00 |
| | | | | 378/41 |
| 2014/0119500 A1* | 5/2014 | Akahori | ................. | A61B 6/584 |
| | | | | 378/17 |

(Continued)

FOREIGN PATENT DOCUMENTS

| | | |
|---|---|---|
| JP | 2018-038908 A | 3/2018 |
| JP | 2022-066616 A | 5/2022 |

*Primary Examiner* — David J Makiya
*Assistant Examiner* — Soorena Kefayati
(74) *Attorney, Agent, or Firm* — SOLARIS Intellectual Property Group, PLLC

(57) ABSTRACT

An information processing apparatus comprising at least one processor, wherein the processor is configured to: acquire a three-dimensional shape of a subject; derive a movement amount of a radiation source that irradiates the subject with radiation based on a difference between a predetermined reference posture and an estimated posture estimated based on the three-dimensional shape for a posture of the subject in a case of capturing a radiation image of the subject; and control the radiation source to move according to the movement amount.

17 Claims, 8 Drawing Sheets

(56) References Cited

U.S. PATENT DOCUMENTS

| | | | |
|---|---|---|---|
| 2015/0003674 A1* | 1/2015 | Eun | A61B 6/08 |
| | | | 382/103 |
| 2015/0223764 A1* | 8/2015 | Kwak | H01J 37/20 |
| | | | 378/63 |
| 2015/0228071 A1* | 8/2015 | Jockel | G06T 7/0012 |
| | | | 382/132 |
| 2015/0313566 A1* | 11/2015 | Diers | A61B 6/505 |
| | | | 378/63 |
| 2016/0220219 A1* | 8/2016 | Lalena | A61B 6/4464 |
| 2017/0020469 A1* | 1/2017 | Lee | A61B 6/4417 |
| 2017/0100089 A1* | 4/2017 | Chang | A61B 6/0492 |
| 2017/0112460 A1* | 4/2017 | Merckx | A61B 6/542 |
| 2017/0119338 A1* | 5/2017 | Merckx | A61B 6/469 |
| 2018/0206810 A1* | 7/2018 | Song | G01B 15/02 |
| 2018/0296178 A1* | 10/2018 | Chang | G06T 7/73 |
| 2018/0338742 A1* | 11/2018 | Singh | A61B 6/587 |
| 2019/0029559 A1* | 1/2019 | Nufer | G01R 33/34092 |
| 2019/0069870 A1* | 3/2019 | Igler | A61B 6/547 |
| 2019/0159740 A1* | 5/2019 | Van Ammel | A61B 6/5241 |
| 2019/0343479 A1* | 11/2019 | Sato | A61B 6/06 |
| 2020/0029916 A1* | 1/2020 | Fieselmann | A61B 6/405 |
| 2020/0029919 A1* | 1/2020 | Senegas | G16H 50/20 |
| 2020/0085385 A1* | 3/2020 | Nye | A61B 6/032 |
| 2020/0100757 A1* | 4/2020 | Senegas | G06T 11/005 |
| 2020/0237332 A1* | 7/2020 | Wang | A61B 6/5241 |
| 2020/0268339 A1* | 8/2020 | Hao | A61B 6/544 |
| 2020/0330055 A1* | 10/2020 | Talgorn | A61B 6/461 |
| 2021/0093284 A1* | 4/2021 | Sutter | A61B 6/547 |
| 2021/0350532 A1* | 11/2021 | Kimmel | A61B 5/721 |
| 2022/0117574 A1* | 4/2022 | Miyake | A61B 6/545 |

* cited by examiner

IMAGING SYSTEM

1

| 10 | 50 | 6 |
|----|----|---|
| IMAGING APPARATUS | CONSOLE | RIS |

FIG. 4

70

| IMAGING METHOD | IMAGING PART | POINT OF VIEW | REFERENCE POSTURE DEFINITION | REFERENCE POSTURE $\theta r$ (DEGREES) | IRRADIATION ANGLE (DEGREES) |
|---|---|---|---|---|---|
| STRYKER METHOD | SHOULDER JOINT | SAGITTAL PLANE | ANGLE FORMED BY STRAIGHT LINE CONNECTING ELBOW AND SHOULDER AND DETECTION SURFACE | 135 | 90 |
| LATERAL RADIOGRAPHY OF THE KNEE JOINT | KNEE JOINT | CORONAL PLANE | ANGLE FORMED BY STRAIGHT LINE CONNECTING KNEE AND ANKLE AND DETECTION SURFACE | 0 (PARALLE) | 90 |
| | | SAGITTAL PLANE | ANGLE FORMED BY STRAIGHT LINE CONNECTING HEEL AND TOE AND DETECTION SURFACE | 90 | 110 |
| ANTHONSEN VIEW | ANKLE JOINT | TRANSVERSE PLANE | ANGLE FORMED BY STRAIGHT LINE CONNECTING HEEL AND TOE AND DETECTION SURFACE | 40 | - |
| | | CORONAL PLANE | ANGLE FORMED BY STRAIGHT LINE CONNECTING KNEE AND ANKLE AND SIDE OF IRRADIATION FIELD SUBSTANTIALLY PARALLEL TO CRANIOCAUDAL DIRECTION | 0 (PARALLE) | - |
| ... | ... | ... | ... | ... | ... |

REFERENCE POSTURE (RAISING 135 DEGREES) IS
NOT BEING TAKEN.
RADIATION SOURCE WILL BE MOVED AND IMAGED
WITHIN STANDARD RANGE (IRRADIATION ANGLE OF
80 TO 90 DEGREES).

REFERENCE POSTURE (RAISING 135 DEGREES) IS
NOT BEING TAKEN.
ALTHOUGH DEPARTING FROM STANDARD RANGE
(IRRADIATION ANGLE OF 80 TO 90 DEGREES),
RADIATION SOURCE WILL BE MOVED AND IMAGED.

REFERENCE POSTURE (RAISING 135 DEGREES) IS
NOT BEING TAKEN.
EVEN RADIATION SOURCE IS MOVED,
APPROPRIATE IMAGING IS NOT POSSIBLE.

FIG. 10

REGARDING STRYKER METHOD

| CLASSIFICATION | THRESHOLD VALUE (ROTATION AMOUNT $\phi$) | NOTIFICATION CONTENT |
|---|---|---|
| 1 | 0 | SUBJECT TAKES REFERENCE POSTURE AND APPROPRIATE IMAGING IS POSSIBLE |
| 2 | 1 TO 10 | SUBJECT DOES NOT TAKE REFERENCE POSTURE AND APPROPRIATE IMAGING IS POSSIBLE WITH MOVEMENT OF RADIATION SOURCE WITHIN STANDARD RANGE |
| 3 | 11 TO 80 | APPROPRIATE IMAGING IS POSSIBLE WITH MOVEMENT OF RADIATION SOURCE BEYOND STANDARD RANGE |
| 4 | 81 OR MORE | APPROPRIATE IMAGING IS NOT POSSIBLE |

INFORMATION PROCESSING APPARATUS, INFORMATION PROCESSING METHOD, AND INFORMATION PROCESSING PROGRAM

CROSS-REFERENCE TO RELATED APPLICATIONS

This application claims priority from Japanese Application No. 2022-158968, filed on Sep. 30, 2022, the entire disclosure of which is incorporated herein by reference.

BACKGROUND

Technical Field

The present disclosure relates to an information processing apparatus, an information processing method, and an information processing program.

Related Art

In radiography of bones, joints, or the like in orthopedic surgery or the like, a subject itself takes a predetermined posture, and then is imaged so that the imaging part can be observed in an appropriate state. For example, in the Stryker method, which is a type of imaging method for the shoulder joint, a posture in which an upper arm is raised at an angle of 135 degrees from an imaging table in a state of a supine position is determined as a posture to be taken by the subject (refer to FIG. 6). A user, such as a doctor or a technician, adjusts the posture of the subject, the position of the radiation source, and the irradiation angle so that the imaging part of the subject can be appropriately imaged (so-called "positioning").

In the related art, various technologies for supporting such positioning in radiography have been known. For example, in JP2018-038908A, it is disclosed that three-dimensional position information of a feature part of a subject is acquired based on an optical image of the subject, and a movement amount of a top plate of an imaging table is calculated and the top plate is moved based on the calculated movement amount such that the feature part of the subject moves to an imaging position based on the position information. In addition, for example, in JP2022-066616A, it is disclosed that pre-imaging with a reduced radiation dose is performed before the main imaging, and the appropriateness of positioning is determined based on a pre-image obtained by the pre-imaging.

By the way, it may be difficult to take a predetermined posture as described above depending on a body shape, a physical ability, an injured state, and the like of the subject. Therefore, there has been a demand for a technology capable of capturing a radiation image such that an imaging part can be appropriately observed even in a case in which the subject does not take a predetermined posture.

SUMMARY

The present disclosure provides an information processing apparatus, an information processing method, and an information processing program capable of capturing a radiation image appropriately.

According to a first aspect of the present disclosure, there is provided an information processing apparatus including at least one processor, in which the processor is configured to acquire a three-dimensional shape of a subject, derive a movement amount of a radiation source that irradiates the subject with radiation based on a difference between a predetermined reference posture and an estimated posture estimated based on the three-dimensional shape for a posture of the subject in a case of capturing a radiation image of the subject, and control the radiation source to move according to the movement amount.

According to a second aspect of the present disclosure, in the first aspect, the processor may be configured to derive a rotation amount of the radiation source about at least one axis as the movement amount.

According to a third aspect of the present disclosure, in the first aspect or the second aspect, the processor may be configured to derive a translation amount of the radiation source in at least one direction as the movement amount.

According to a fourth aspect of the present disclosure, in any one of the first aspect to the third aspect, the processor may be configured to derive a rotation amount of the radiation source about at least one axis and a translation amount of the radiation source in at least one direction, as the movement amount.

According to a fifth aspect of the present disclosure, in any one of the first aspect to the fourth aspect, the processor may be configured to perform a notification in a case in which the derived movement amount exceeds a predetermined threshold value.

According to a sixth aspect of the present disclosure, in the fifth aspect, a plurality of threshold values may be provided stepwise as the threshold value, and the processor may be configured to determine a classification by comparing the derived movement amount with the plurality of threshold values and notify of contents according to the classification.

According to a seventh aspect of the present disclosure, in the fifth aspect or the sixth aspect, the processor may be configured to notify whether or not the movement amount is within a predetermined standard range.

According to an eighth aspect of the present disclosure, in any one of the fifth aspect to the seventh aspect, the processor may be configured to notify that it is incapable of capturing the radiation image appropriately.

According to a ninth aspect of the present disclosure, in any one of the first aspect to the eighth aspect, the processor may be configured to specify a joint point of the subject based on the three-dimensional shape, and estimate the estimated posture using the joint point.

According to a tenth aspect of the present disclosure, in any one of the first aspect to the ninth aspect, the reference posture may be predetermined for each imaging method according to an imaging part, and the processor may be configured to receive a designation of the imaging method, and derive the movement amount based on a difference between the reference posture corresponding to the designated imaging method and the estimated posture.

According to an eleventh aspect of the present disclosure, in the tenth aspect, in a case in which the imaging method is a Stryker method, the reference posture and the estimated posture may be determined by an angle formed by a straight line connecting an elbow and a shoulder of the subject and a detection surface of the radiation.

According to a twelfth aspect of the present disclosure, in the tenth aspect, in a case in which the imaging method is a lateral radiography of the knee joint, the reference posture and the estimated posture may be determined by an angle formed by a straight line connecting a knee and an ankle of the subject and a detection surface of the radiation.

According to a thirteenth aspect of the present disclosure, in the tenth aspect, in a case in which the imaging method is an Anthonsen view, the reference posture and the estimated posture may be determined by an angle formed by a straight line connecting a heel and a toe of the subject in a sagittal plane and a detection surface of the radiation, an angle formed by a straight line connecting the heel and the toe of the subject in a transverse plane and the detection surface of the radiation, and an angle formed by a straight line connecting a knee and an ankle of the subject and a side of an irradiation field substantially parallel to a craniocaudal direction of the subject.

According to a fourteenth aspect of the present disclosure, in any one of the first aspect to the thirteenth aspect, the processor may be configured to acquire the three-dimensional shape measured by a distance-measuring sensor using laser light with 64 rows or more and 512 rows or less.

According to a fifteenth aspect of the present disclosure, in any one of the first aspect to the thirteenth aspect, the processor may be configured to acquire the three-dimensional shape measured by a time of flight (TOF) camera.

According to a sixteenth aspect of the present disclosure, in any one of the first aspect to the thirteenth aspect, the processor may be configured to acquire the three-dimensional shape measured by a stereo camera.

According to a seventeenth aspect of the present disclosure, there is provided an information processing method including acquiring a three-dimensional shape of a subject, deriving a movement amount of a radiation source that irradiates the subject with radiation based on a difference between a predetermined reference posture and an estimated posture estimated based on the three-dimensional shape for a posture of the subject in a case of capturing a radiation image of the subject, and controlling the radiation source to move according to the movement amount.

According to an eighteenth aspect of the present disclosure, there is provided an information processing program for causing a computer to execute a process including acquiring a three-dimensional shape of a subject, deriving a movement amount of a radiation source that irradiates the subject with radiation based on a difference between a predetermined reference posture and an estimated posture estimated based on the three-dimensional shape for a posture of the subject in a case of capturing a radiation image of the subject, and controlling the radiation source to move according to the movement amount.

With the above-described aspects, the information processing apparatus, the information processing method, and the information processing program according to the present disclosure are capable of capturing a radiation image appropriately.

BRIEF DESCRIPTION OF THE DRAWINGS

FIG. 4 is a view illustrating an example of reference posture information.

FIG. 7 is a view illustrating an example of a notification displayed on a display.

FIG. 8 is a view illustrating an example of a notification displayed on the display.

FIG. 9 is a view illustrating an example of a notification displayed on the display.

FIG. 10 is a view illustrating an example of notification contents for each classification.

DETAILED DESCRIPTION

Figures 1, 2:
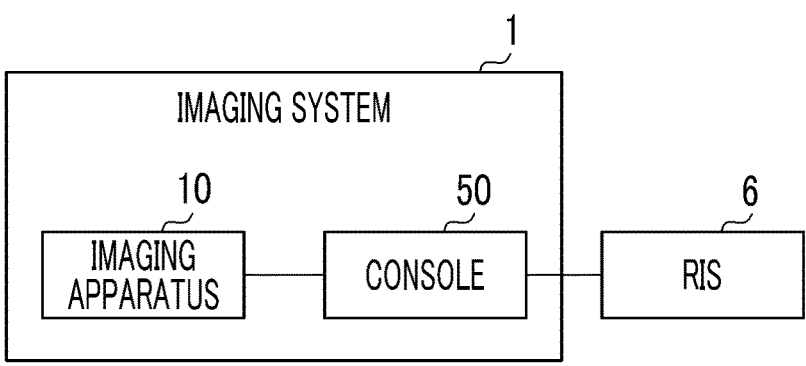
FIG. 1 is a view illustrating an example of a schematic configuration of an imaging system.
FIG. 2 is a side view illustrating an example of an external appearance of an imaging apparatus.

In the following, embodiments of the present disclosure will be explained with reference to the drawings. First, a configuration of an imaging system 1 will be explained with reference to FIG. 1. FIG. 1 is a diagram illustrating a schematic configuration of the imaging system 1. As illustrated in FIG. 1, the imaging system 1 comprises an imaging apparatus 10 and a console 50. The imaging apparatus 10 and the console 50, and the console 50 and an external radiology information system (RIS) 6 are configured to be connectable to each other via a wired or wireless network.

The console 50 acquires an imaging order or the like from the RIS 6 and controls the imaging apparatus 10 according to the acquired imaging order, an instruction from a user, and the like. The imaging apparatus 10 captures a radiation image of a subject according to the control of the console 50. The console 50 is an example of an information processing apparatus of the present disclosure.

Next, the imaging apparatus 10 will be explained with reference to FIG. 2. FIG. 2 is a diagram illustrating a schematic configuration of the imaging apparatus 10, and is a side view illustrating a case in which the imaging apparatus 10 is seen from the right side of a subject H. As illustrated in FIG. 2, the imaging apparatus 10 comprises a radiation emitting unit 12, an imaging table 16, a radiation detector 20, a control device 24, and a distance-measuring sensor 28. In the imaging apparatus 10, a user, such as a doctor or a technician, positions an imaging part of the subject H to be appropriately imaged on an imaging surface 16A of the imaging table 16.

The radiation emitting unit 12 comprises a radiation source 13 that emits radiation R such as X-rays. In addition, the radiation emitting unit 12 comprises a collimator (not illustrated) and the like, and is configured to change an irradiation field of the radiation R emitted from the radiation source 13.

In addition, the radiation emitting unit 12 is held by a support column 14 suspended from a ceiling of an imaging room. The support column 14 is attached to rails running around the ceiling via wheels (not illustrated), and is movable in a horizontal direction (X direction and Y direction) in the imaging room. In addition, the support column 14 can be expanded and contracted in a vertical direction (Z direction). In addition, the imaging apparatus 10 comprises a moving mechanism (not illustrated) such as a motor that moves the support column 14 in the horizontal direction and expands and contracts it in the vertical direction. By the movement of the support column 14 in the horizontal direction and the expansion and contraction of the support column 14 in the vertical direction, the radiation emitting unit 12 is also translationally moved in the horizontal direction and the vertical direction.

In addition, the radiation emitting unit 12 is connected to the support column 14 so as to be rotationally movable and is rotationally movable about a rotation axis α extending in the horizontal direction (X direction at a position in FIG. 2). As a result, it becomes possible to perform oblique imaging in which the radiation R is emitted in an inclined manner toward a head direction or a foot direction of the subject H. In addition, the radiation emitting unit 12 is rotationally movable about a rotation axis (3 (that is, about the support column 14) extending in the vertical direction (Z direction). As a result, the registration with respect to the imaging part of the subject H becomes possible. In addition, the imaging apparatus 10 comprises a rotation mechanism (not illustrated) such as a motor that rotationally moves the radiation emitting unit 12 about the rotation axis α and the rotation axis (3.

The imaging table 16 is an imaging table for performing the radiography of the subject H in a decubitus posture. The radiation detector 20 is built in a top plate of the imaging table 16. The radiation detector 20 detects the radiation R transmitted through the subject H and the top plate of the imaging table 16 on a detection surface 20A, generates a radiation image based on the detected radiation R, and outputs image data indicating the generated radiation image.

The type of the radiation detector 20 is not particularly limited. For example, the radiation detector 20 may be an indirect conversion type radiation detector that converts the radiation R into light and converts the converted light into electric charge, or may be a direct conversion type radiation detector that directly converts the radiation R into electric charge. In addition, for example, the radiation detector 20 may include a cassette that is detachably accommodated and may be movable along a long side direction (Y direction) of the imaging table 16 by a slide mechanism (not illustrated). In addition, for example, the radiation detector 20 may have a size corresponding to substantially the entire surface of the top plate of the imaging table 16, and may be accommodated in a non-detachable manner.

The control device 24 controls the entire operation of the imaging apparatus 10 according to instructions from the console 50 and the user. Specifically, the control device 24 performs movement control of the radiation emitting unit 12 in the horizontal direction and the vertical direction, rotation control about the rotation axis α and the rotation axis (3, and irradiation control of the radiation R (for example, the setting tube voltage, the tube current, the irradiation time, and the like).

In addition, the control device 24 acquires image data indicating the radiation image generated by the radiation detector 20 and outputs the image data to the console 50. In addition, the control device 24 acquires a three-dimensional shape of the subject H measured by the distance-measuring sensor 28 and outputs the three-dimensional shape to the console 50.

The control device 24 is composed of, for example, a central processing unit (CPU), a read only memory (ROM), a random access memory (RAM), a storage medium, an interface (I/F) unit, and an operating unit, which are not illustrated. The control device 24 exchanges various types of information with the console 50 via the I/F unit.

The distance-measuring sensor 28 is a sensor for acquiring at least a three-dimensional shape of an imaging part of the subject H. As illustrated in FIG. 2, for example, the distance-measuring sensor 28 may be attached to substantially the same surface as an irradiation opening of the radiation R of the radiation emitting unit 12, or may be attached to the support column 14, the ceiling of the imaging room, or the like.

As the distance-measuring sensor 28, for example, laser imaging detection and ranging or light detection and ranging (LIDAR), a time of flight (TOF) camera, a stereo camera, or the like can be applied. In the LIDAR and TOF cameras, the subject H is irradiated with light such as infrared rays and visible light, and a distance to the subject H is measured based on a time until the subject H receives the reflected light or a phase change between the emitted light and the received light. The LIDAR measures the three-dimensional shape of the subject H by disposing a plurality of laser light emitters in a vertical direction and horizontally scanning (rotating) each of the emitters. The TOF camera measures the three-dimensional shape of the subject H by irradiating the subject H with diffuse light. The stereo camera measures the three-dimensional shape of the subject H by using the principle of triangulation based on a plurality of images obtained by imaging the subject H from different directions.

From the viewpoint of privacy protection, as the distance-measuring sensor 28, in particular, it is preferable to use the LIDAR using laser light with 64 or more rows and 512 rows or less (that is, the laser light emitters are disposed in the vertical direction in 64 or more rows and 512 or less rows and each performs horizontal scanning). By setting the number of rows to 64 or more, the three-dimensional shape of the subject H can be acquired with sufficient accuracy, and by setting the number of rows to 512 or less, the roughness can be made to such an extent that an individual of the subject H cannot be specified.

By the way, in radiography of bones, joints, or the like in orthopedic surgery or the like, the subject H itself takes a predetermined posture (hereinafter, referred to as "reference posture"), and then is imaged so that the imaging part can be observed in an appropriate state. For example, in the Stryker method, which is a type of imaging method for the shoulder joint, a posture in which an upper arm is raised at an angle of 135 degrees from the imaging table 16 in a state of a supine position is determined as a reference posture to be taken by the subject H (refer to FIG. 6).

On the other hand, it may be difficult to take such a reference posture depending on the body shape, physical ability, injured state, and the like of the subject H. Therefore, in the console 50 according to the present embodiment, the irradiation position and the irradiation angle of the radiation R are controlled according to the posture of the subject H, so that even in a case in which the subject H does not take the reference posture, the console 50 supports the capturing of the radiation image so that the imaging part can be appropriately observed. In the following, the console 50 will be explained.

Figure 3:
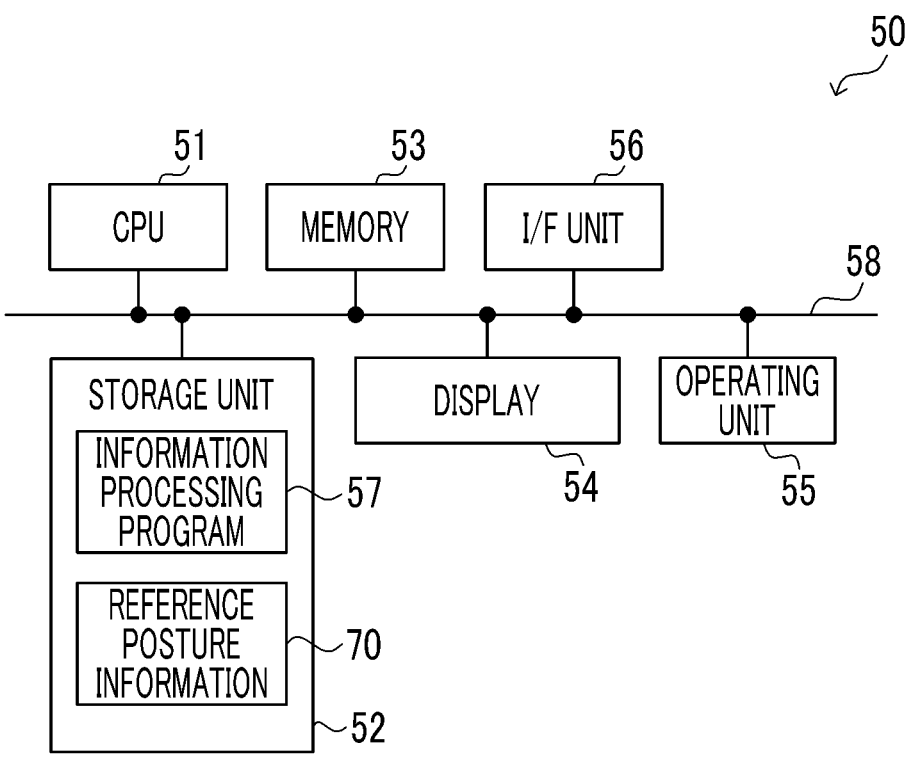
FIG. 3 is a block diagram illustrating an example of a hardware configuration of a console.

First, an example of a hardware configuration of the console 50 will be explained with reference to FIG. 3. As illustrated in FIG. 3, the console 50 includes a central processing unit (CPU) 51, a non-volatile storage unit 52, and a memory 53 as a temporary storage region. In addition, the console 50 includes a display 54 such as a liquid crystal display, an operating unit 55 such as a touch panel, a keyboard, and a mouse, and an interface (I/F) unit 56. The I/F unit 56 performs wired or wireless communication with the imaging apparatus 10, the RIS 6, and other external devices. The CPU 51, the storage unit 52, the memory 53, the display 54, the operating unit 55, and the I/F unit 56 are connected to each other via a bus 58 such as a system bus and a control bus such that various types of information can be exchanged.

The storage unit 52 is realized by, for example, a storage medium such as a hard disk drive (HDD), a solid state drive (SSD), and a flash memory. In the storage unit 52, an information processing program 57 in the console 50 is stored. The CPU 51 reads out the information processing program 57 from the storage unit 52, develops the information processing program 57 into the memory 53, and executes the developed information processing program 57. The CPU 51 is an example of a processor of the present disclosure. For example, a personal computer, a server computer, a smartphone, a tablet terminal, a wearable terminal, or the like can be appropriately applied as the console 50.

In addition, in the storage unit 52, reference posture information 70 is stored. FIG. 4 illustrates an example of the reference posture information 70. As illustrated in FIG. 4, the reference posture information 70 is predetermined for each imaging method according to an imaging part, for example, a shoulder joint, a knee joint, and an ankle joint. Specifically, for each imaging method, the reference posture to be taken by the subject H is determined by the angle.

Figure 5:
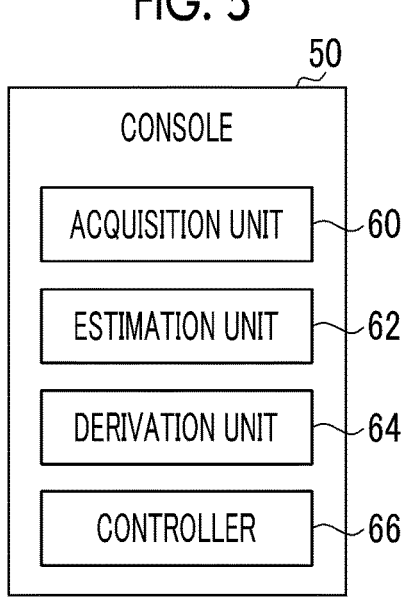
FIG. 5 is a block diagram illustrating an example of a functional configuration of the console.

Next, an example of a functional configuration of the console 50 will be explained with reference to FIG. 5. As illustrated in FIG. 5, the console 50 includes an acquisition unit 60, an estimation unit 62, a derivation unit 64, and a controller 66. In a case in which the CPU 51 executes the information processing program 57, the CPU 51 functions as each functional unit of the acquisition unit 60, the estimation unit 62, the derivation unit 64, and the controller 66.

Example 1

Figure 6:
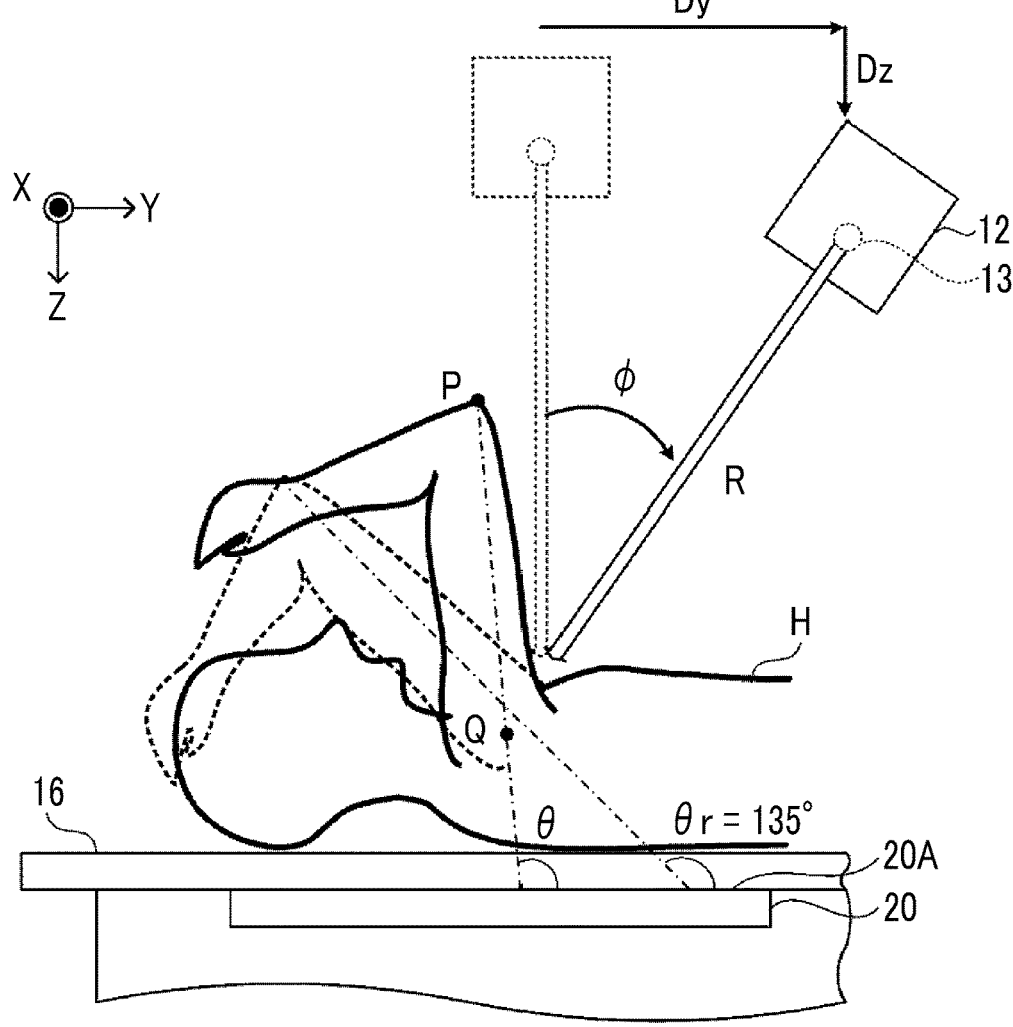
FIG. 6 is a schematic view illustrating a state of imaging by the Stryker method.

In the following, with reference to FIG. 6, the functions of each functional unit will be explained using an example in which imaging is performed by the Stryker method, which is a type of imaging method for the shoulder joint. FIG. 6 is a schematic view illustrating a state in which a right shoulder joint of the subject H is imaged by the Stryker method, and is a side view of a case in which the imaging apparatus 10 is seen from the right side of the subject H. In FIG. 6, the reference posture in the Stryker method is illustrated by a dotted line, and the posture actually taken by the subject H is illustrated by a solid line. The reference posture of the Stryker method is a posture in which the upper arm is raised at an angle of 135 degrees from the imaging table 16 in a state of a supine position. In addition, the radiation R is emitted perpendicularly to the detection surface 20A from a position at a distance of 100 cm toward an axilla of the subject H.

The acquisition unit 60 acquires the three-dimensional shape of the subject H measured by the distance-measuring sensor 28 of the imaging apparatus 10. For example, the acquisition unit 60 acquires the three-dimensional shape of the subject H illustrated by the solid line in FIG. 6. The acquisition unit 60 may acquire at least the three-dimensional shape including the imaging part. For example, in the Stryker method, a three-dimensional shape including at least a portion of the shoulder joint may be acquired.

In addition, the acquisition unit 60 receives a designation of the imaging method in which the imaging is being performed. For example, the acquisition unit 60 may acquire an imaging order including the designation of the imaging method from the RIS 6. In addition, for example, the acquisition unit 60 may receive the designation of the imaging method by the user via the operating unit 55.

The estimation unit 62 estimates the posture taken by the subject H, based on the three-dimensional shape of the subject H acquired by the acquisition unit 60. In the following, the posture estimated by the estimation unit 62 to be taken by the subject H is referred to as an "estimated posture". Specifically, the estimation unit 62 specifies a joint point of the subject H and estimates the estimated posture using the specified joint point. Here, the joint point specified by the estimation unit 62 corresponds to the designated imaging method (refer to FIG. 4).

For example, in a case in which the imaging method is the Stryker method as illustrated in FIG. 6, the estimation unit 62 specifies an elbow P and a shoulder Q of the subject H as joint points. Then, an angle $\theta$ formed by a straight line connecting the elbow P and the shoulder Q of the subject H and the detection surface 20A of the radiation (an upper surface of the radiation detector 20) is estimated as the estimated posture. As a method for specifying the joint point, known technologies can be appropriately applied.

The derivation unit 64 derives a movement amount of the radiation source 13 that irradiates the subject H with the radiation R, based on a difference between a predetermined reference posture and an estimated posture estimated by the estimation unit 62 for the posture of the subject H in a case of capturing the radiation image of the subject H. Specifically, the derivation unit 64 refers to the reference posture information 70 and derives the movement amount based on a difference between the reference posture corresponding to the designated imaging method and the estimated posture.

Here, the movement amount derived by the derivation unit 64 may be a rotation amount of the radiation source 13 about at least one axis. For example, the derivation unit 64 may derive the rotation amount about the rotation axis $\alpha$ and/or the rotation axis $\beta$ for the radiation emitting unit 12 of FIG. 2. In addition, for example, the movement amount derived by the derivation unit 64 may be a translation amount of the radiation source 13 in at least one direction. For example, the derivation unit 64 may derive the translation amount in the X direction, the Y direction, and/or the Z direction for the radiation emitting unit 12 of FIG. 2. In addition, for example, the derivation unit 64 may derive the above-described rotation amount and translation amount by appropriately combining them.

For example, in a case in which the imaging method is the Stryker method as illustrated in FIG. 6, the derivation unit 64 may incline the radiation source 13 in a caudal direction (the $\varphi$ direction in FIG. 6) by the difference between the reference posture and the estimated posture. For example, it is assumed that a reference posture Or is 135 degrees as determined in the reference posture information 70 of FIG. 4 and an estimated posture $\theta$ estimated by the estimation unit 62 is 95 degrees. In this case, since a difference $(\theta r - \theta)$ between them is 40 degrees, the derivation unit 64 may derive a rotation amount $\varphi$ of the radiation source 13 about the rotation axis $\alpha$ to be 40 degrees in the caudal direction.

In addition, in a case in which the radiation source 13 is rotated by 40 degrees about the rotation axis $\alpha$ without the translational movement, since the radiation R is emitted with a deviation toward a direction of the head of the subject H instead of the axilla, it is necessary to translationally move the radiation source 13 to a position where the radiation R is appropriately emitted to the axilla. Therefore, for example, the derivation unit 64 may specify the position of the axilla based on the three-dimensional shape, and derive a translation amount Dy in the Y direction and a translation amount Dz in the Z direction so as to move the radiation source 13 on a circumference with a radius of 100 cm (corresponding to a predetermined distance between the radiation source 13 and the axilla) centered on the axilla.

The controller 66 controls the radiation source 13 to move according to the movement amount derived by the derivation unit 64. That is, the controller 66 gives an instruction to the control device 24 of the imaging apparatus 10 to rotate the radiation source 13 by the rotation amount φ, moves the radiation source 13 by the translation amount Dy in the Y direction, and moves the radiation source 13 by the translation amount Dz in the Z direction.

In addition, the controller 66 may perform a notification in a case in which the movement amount derived by the derivation unit 64 exceeds a predetermined threshold value. For example, with respect to the irradiation angle of the radiation R, a reference value is determined as illustrated in the reference posture information 70 of FIG. 4, but in an actual imaging site, a user such as a doctor or a technician may appropriately adjust it according to the body shape of the subject H or the like. Therefore, in the guideline for the imaging method or the like, a standard range, which allows variations in the irradiation angle of the radiation R or the like, may be determined. For example, with respect to the Stryker method, the optimum irradiation angle of the radiation R is 90 degrees from the detection surface 20A, but it is also standardly permitted to incline it about 80 degrees (that is, 10 degrees as the rotation amount φ) from the detection surface 20A.

Therefore, the controller 66 may notify whether or not the movement amount derived by the derivation unit 64 is within a standard range predetermined in the guidelines or the like. Specifically, an upper limit and/or a lower limit of the allowable range predetermined in the guidelines or the like may be set in advance as a threshold value, and the controller 66 may determine whether or not the movement amount derived by the derivation unit 64 exceeds the threshold value and perform a notification according to the determination result.

For example, in a case in which the movement amount derived by the derivation unit 64 satisfies the standard range, the controller 66 may perform a control to display a screen D1 on the display 54 as illustrated in FIG. 7. The screen D1 notifies that although the subject H does not take the reference posture, the radiation source 13 is moved within the standard range and appropriate imaging is possible. On the other hand, in a case in which the movement amount derived by the derivation unit 64 does not satisfy the standard range, the controller 66 may perform a control to display a screen D2 on the display 54 as illustrated in FIG. 8. The screen D2 notifies that although the subject H does not take the reference posture and the radiation source 13 moves beyond the standard range, appropriate imaging is possible.

In addition, no matter how the radiation source 13 is moved, it may be difficult to capture the radiation image such that an imaging part can be appropriately observed. For example, in a case of imaging by the Stryker method, in a case in which the subject H can hardly raise the upper arm, even if the irradiation angle and the position of the radiation source 13 are adjusted, appropriate imaging is difficult because other portions such as the elbow overlap the shoulder joint. In addition, for example, in imaging by the Stryker method, even if an attempt is made to rotate and translationally move the radiation source 13 on a circumference with a radius of 100 cm centered on the axilla as described above, in a case in which the movement amount is too large, a housing of the radiation emitting unit 12 cannot be moved because it interferes with the subject H, the imaging table 16, and the like.

Therefore, the controller 66 may notify that the radiation image cannot be appropriately captured. Specifically, an upper limit and/or a lower limit of the movement amount that is capable of performing appropriate imaging based on a human body structure and/or a mechanical constraint of the imaging apparatus 10 may be set in advance as a threshold value. For example, in a case in which the movement amount derived by the derivation unit 64 exceeds a threshold value set based on the human body structure and/or the mechanical constraint of the imaging apparatus 10, the controller 66 performs a control to display a screen D3 as illustrated in FIG. 9 on the display 54. The screen D3 notifies that the subject H does not take the reference posture, and even if the radiation source 13 is moved, the radiation image cannot be appropriately captured.

In addition, each of the above-described threshold values and notification contents may be combined appropriately. For example, as illustrated in FIG. 10, a plurality of threshold values are set in advance stepwise as threshold values, and the controller 66 may determine the classification by comparing the movement amount derived by the derivation unit 64 with the plurality of threshold values, and may notify of contents according to the classification. The threshold values, the classification method, and the notification contents may be predetermined for each imaging method, for example, and may be stored in the storage unit 52. As illustrated in FIG. 10, in a case in which the subject H takes the reference posture and appropriate imaging can be performed without moving the radiation source 13 (that is, a case in which the movement amount derived by the derivation unit 64 is 0), the controller 66 may notify that fact.

The means for notification is not limited to the display on the display 54. For example, the controller 66 may perform the notification using a voice from a speaker provided in the console 50 and/or the imaging apparatus 10. In addition, for example, the controller 66 may perform the notification by blinking a lamp provided in the console 50 and/or the imaging apparatus 10. In addition, a timing of the notification may be before or after the radiography.

Example 2

Although the functions of the respective functional units have been explained above with reference to an example of performing imaging by the Stryker method, the console 50 according to the present embodiment can be applied to other imaging methods. As an example, an example of performing imaging by a lateral radiography of the knee joint, which is a type of imaging method for the knee joint, will be explained with reference to FIG. 11.

Figure 11:
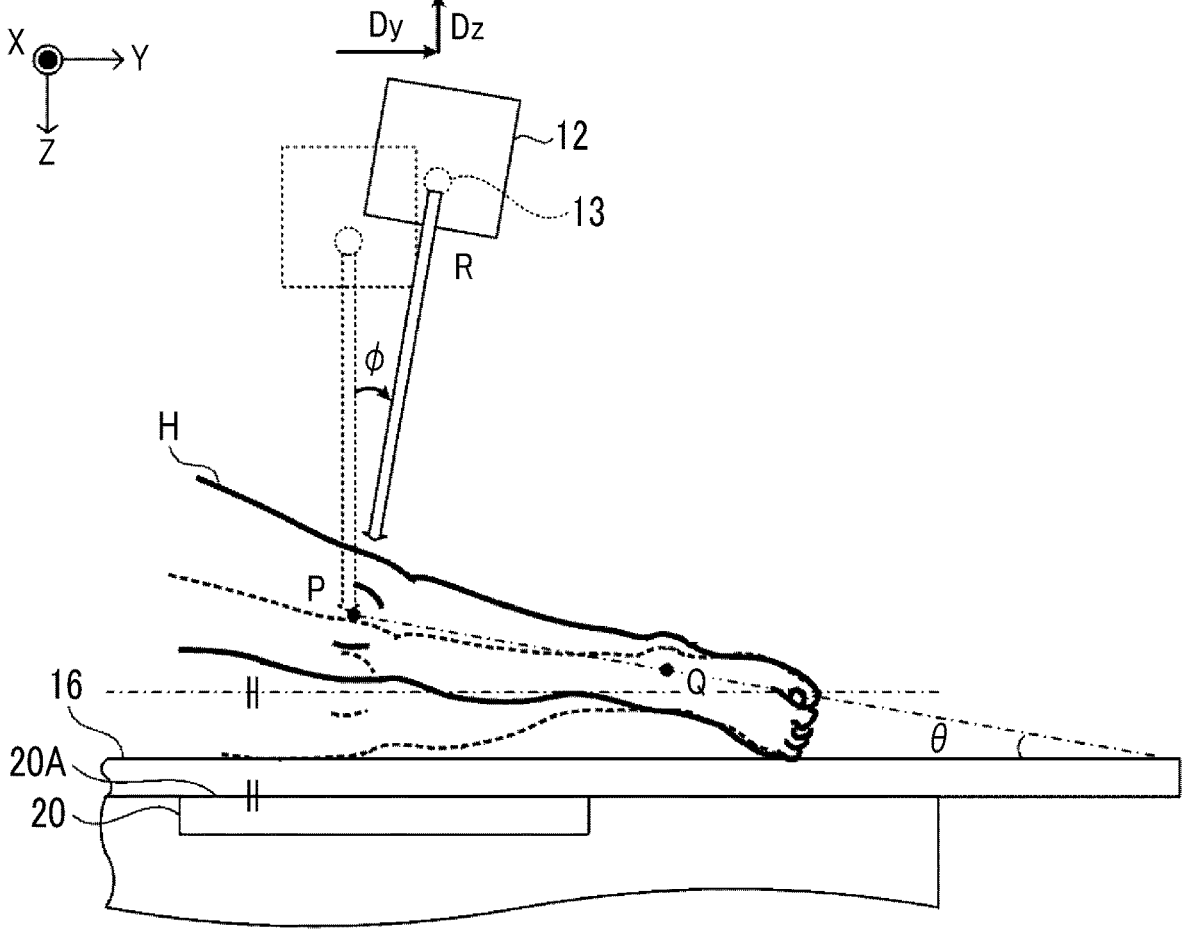
FIG. 11 is a schematic view illustrating a state of imaging by the lateral radiography of the knee joint.

FIG. 11 is a schematic view illustrating a state in which a right knee joint of the subject H is imaged by a lateral radiography of the knee joint. In FIG. 11, the reference posture in the lateral radiography of the knee joint is illustrated by a dotted line, and the posture actually taken by the subject H is illustrated by a solid line. The reference posture of the lateral radiography of the knee joint is a posture in which a straight line connecting the knee and the ankle is substantially horizontal in a lateral decubitus position with the leg to be imaged (the right leg in FIG. 11) downward. In addition, the radiation R is emitted perpendicularly to the detection surface 20A from a position at a distance of 100 cm toward the knee of the subject H.

On the other hand, depending on a physique of the subject H or the like, the knee may float, and it may be difficult to make the straight line connecting the knee and the ankle substantially horizontal. Therefore, the estimation unit 62 specifies a knee P and an ankle Q of the subject H as joint points based on the three-dimensional shape of the subject H acquired by the acquisition unit 60. Then, the estimation unit 62 estimates an angle $\theta$ formed by the straight line connecting the knee P and the ankle Q of the specified subject H and the detection surface 20A of the radiation R as the estimated posture.

The derivation unit 64 derives the movement amount such that the radiation source 13 is inclined in the caudal direction (the $\varphi$ direction in FIG. 11) by a difference between the reference posture and the estimated posture. For example, it is assumed that the reference posture $\theta$r is 0 degrees and the estimated posture $\theta$ estimated by the estimation unit 62 is 10 degrees as determined in the reference posture information 70 of FIG. 4. In this case, since a difference ($\theta$r−$\theta$) between them is 10 degrees, the derivation unit 64 may derive a rotation amount $\varphi$ of the radiation source 13 about the rotation axis $\alpha$ to be 10 degrees in the caudal direction.

In addition, in a case in which the radiation source 13 is rotated by 10 degrees about the rotation axis $\alpha$ without the translational movement, since the radiation R is emitted with a deviation toward a direction of the head of the subject H instead of the knee, it is necessary to translationally move the radiation source 13 to a position where the radiation R is appropriately emitted to the knee. Therefore, for example, the derivation unit 64 may specify the position of the knee based on the three-dimensional shape, and derive a translation amount Dy in the Y direction and a translation amount Dz in the Z direction so as to move the radiation source 13 on a circumference with a radius of 100 cm (corresponding to a predetermined distance between the radiation source 13 and the knee) centered on the knee.

Example 3

Figure 12:
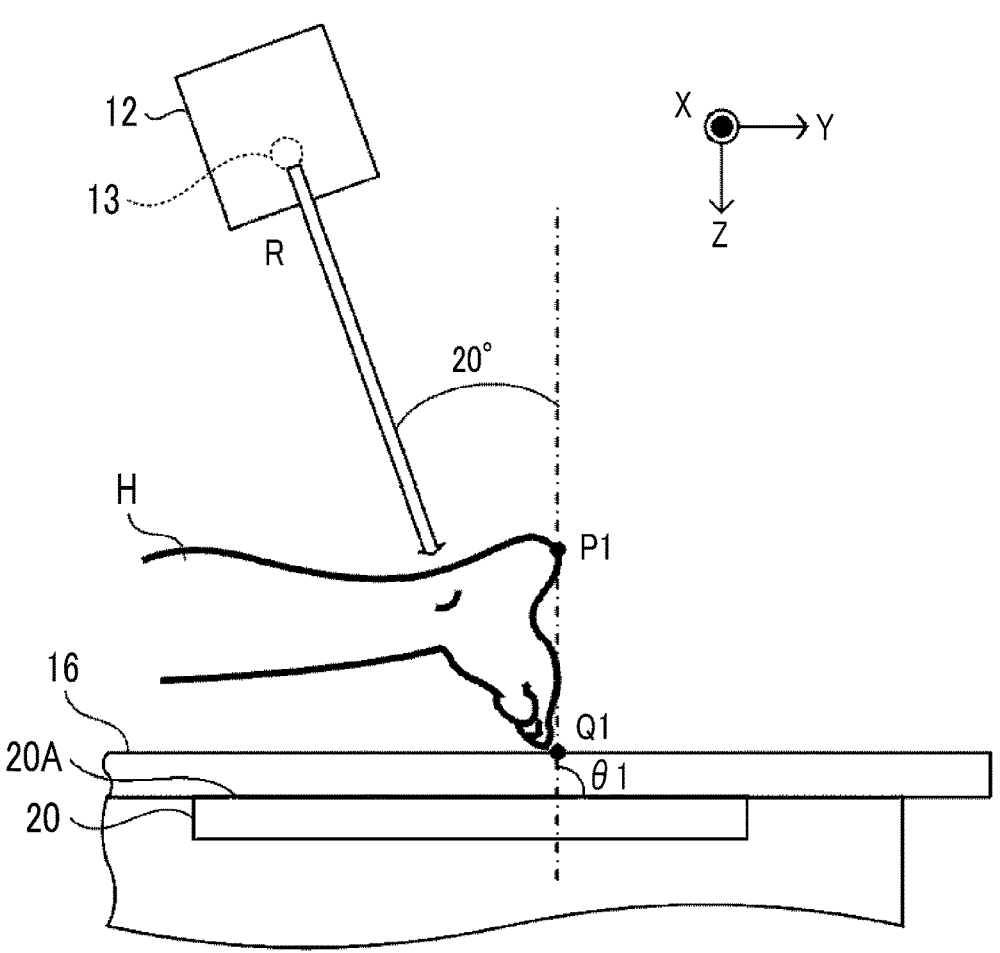
FIG. 12 is a schematic view illustrating a state of imaging by the Anthonsen view.
Figure 13:
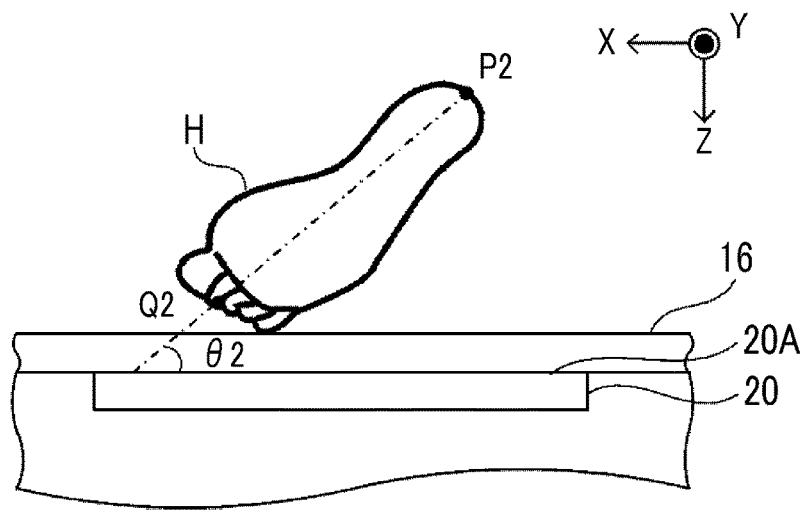
FIG. 13 is a schematic view illustrating a state of imaging by the Anthonsen view.
Figure 14:
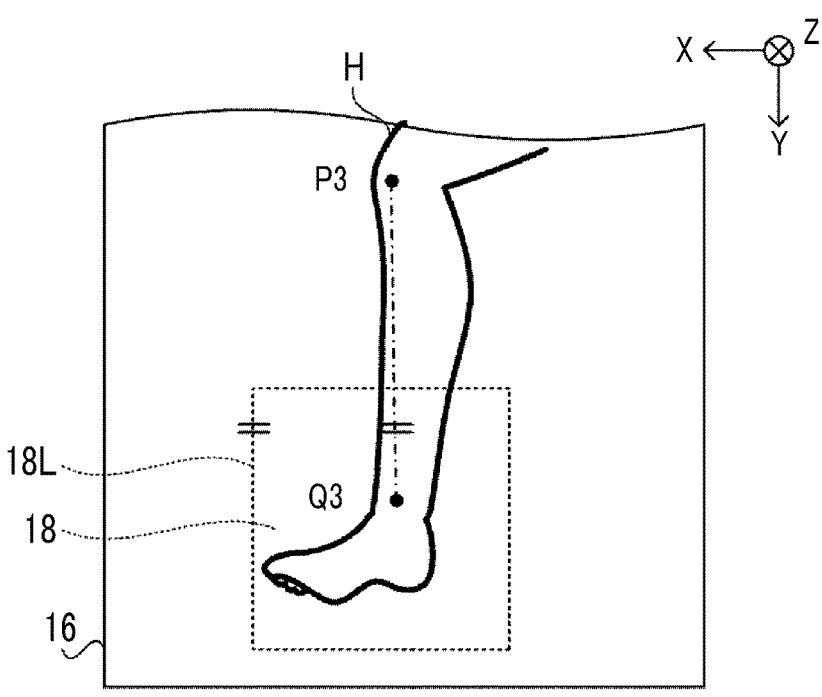
FIG. 14 is a schematic view illustrating a state of imaging by the Anthonsen view.

Next, an example of performing imaging by the Anthonsen view, which is a type of imaging method for the ankle joint, will be explained with reference to FIG. 12 to FIG. 14. FIG. 12 to FIG. 14 are schematic views illustrating a state in which the right ankle joint of the subject H is imaged by the Anthonsen view, respectively. FIG. 12 is a view of the subject H seen from the side, FIG. 13 is a view of the subject H seen from a sole side, and FIG. 14 is a bird's-eye view of the subject H. In FIG. 12 to FIG. 14, the reference posture of the subject H is illustrated by a solid line. The reference posture of the Anthonsen view is from the lateral decubitus position in which the straight line connecting a knee P3 and an ankle P3 and a side 18L of an irradiation field 18 are substantially parallel as illustrated in FIG. 14, to the standing posture with the foot so that a sole surface is perpendicular to the detection surface 20A as illustrated FIG. 12 and an angle formed by the straight line connecting the heel and the toe and the detection surface 20A is 40 degrees as illustrated in FIG. 13. In addition, the radiation R is emitted from a position at a distance of 100 cm toward a medical malleolus of the subject H, with an inclination of 20 degrees in a craniocaudal direction with respect to the perpendicular line of the detection surface 20A (that is, at an angle of 110 degrees from the detection surface 20A) (refer to FIG. 12).

Since the positioning of the Anthonsen view is complicated as described above, the estimation unit 62 estimates a plurality of parameters related to the estimated postures based on the three-dimensional shape of the subject H. The derivation unit 64 derives the movement amount of the radiation source 13 based on each of the parameters.

First, as illustrated in FIG. 13, the estimation unit 62 specifies a heel P2 and a toe Q2 of the subject H in a transverse plane based on the three-dimensional shape of the subject H acquired by the acquisition unit 60. Then, the estimation unit 62 estimates an angle $\theta$2 formed by the straight line connecting the heel P2 and the toe Q2 of the subject H in the specified transverse plane and the detection surface 20A of the radiation R.

As determined in the reference posture information 70 of FIG. 4, the reference posture $\theta$r related to the straight line connecting the heel P2 and the toe Q2 of the subject H in the transverse plane is 40 degrees. Here, it is desired that the angle formed by the straight line connecting the heel P2 and the toe Q2 of the subject H in the transverse plane and the detection surface 20A of the radiation R is always 40 degrees. Therefore, in a case in which the angle $\theta$2 estimated by the estimation unit 62 does not satisfy 40 degrees, the controller 66 may notify that fact and wait until the angle $\theta$2 reaches 40 degrees.

Second, as illustrated in FIG. 12, the estimation unit 62 specifies a heel P1 and a toe Q1 of the subject H in a sagittal plane based on the three-dimensional shape of the subject H acquired by the acquisition unit 60. Then, the estimation unit 62 estimates an angle $\theta$1 formed by a straight line (that is, a sole surface) connecting a heel P1 and a toe Q1 of the subject H in the specified sagittal plane and the detection surface 20A of the radiation R.

The derivation unit 64 derives the movement amount such that the irradiation angle of the radiation source 13 is changed by a difference between the reference posture $\theta$r and the estimated posture $\theta$1. As determined in the reference posture information 70 of FIG. 4, the reference posture $\theta$r related to the straight line connecting the heel P1 and the toe Q1 of the subject H in the sagittal plane is 90 degrees. In addition, the radiation R is emitted at an angle of 110 degrees from the detection surface 20A (that is, inclined by 20 degrees in the craniocaudal direction with respect to the perpendicular line of the detection surface 20A). For example, in a case in which the estimated posture $\theta$1 estimated by the estimation unit 62 is 80 degrees, since the difference ($\theta$r−$\theta$1) between the reference posture and the estimated posture is 10 degrees, the derivation unit 64 may derive the rotation amount $\varphi$ of the radiation source 13 about the rotation axis $\alpha$ to be 10 degrees in the caudal direction. That is, the radiation R may be emitted at an angle of 100 degrees from the detection surface 20A (that is, inclined by 10 degrees in the craniocaudal direction with respect to the perpendicular line of the detection surface 20A).

In addition, for example, in a case in which the estimated posture $\theta$1 estimated by the estimation unit 62 is 100 degrees, since the difference ($\theta$r−$\theta$1) between the reference posture and the estimated posture is −10 degrees, the derivation unit 64 may derive the rotation amount $\varphi$ of the radiation source 13 about the rotation axis $\alpha$ to be 10 degrees in the craniocaudal direction. That is, the radiation R may be emitted at an angle of 120 degrees from the detection surface 20A (that is, inclined by 30 degrees in the craniocaudal direction with respect to the perpendicular line of the detection surface 20A).

Third, as illustrated in FIG. 14, the estimation unit 62 specifies a knee P3 and an ankle Q3 of the subject H in a coronal plane based on the three-dimensional shape of the subject H acquired by the acquisition unit 60. Then, the estimation unit 62 estimates an angle $\theta$3 formed by a straight line connecting the knee P3 and the ankle Q3 of the subject H on the specified coronal plane and the side 18L of the irradiation field 18 substantially parallel to the craniocaudal direction (the Y direction) of the subject H.

The derivation unit 64 derives the movement amount such that the irradiation angle of the radiation source 13 is changed by a difference between the reference posture θr and the estimated posture θ3. As determined in the reference posture information 70 of FIG. 4, a reference posture θr related to the angle formed by the straight line connecting the knee P3 and the ankle Q3 of the subject H on the coronal plane and the side 18L of the irradiation field 18 substantially parallel to the craniocaudal direction (the Y direction) of the subject H is 0 degrees (parallel). For example, in a case in which the estimated posture θ3 estimated by the estimation unit 62 is 20 degrees, a difference (θr−θ3) between the reference posture and the estimated posture is −20 degrees. In this case, the derivation unit 64 may derive the rotation amount of the radiation source 13 about the rotation axis β to be 20 degrees. That is, by rotating the radiation source 13 about the rotation axis β by 20 degrees and inclining the irradiation field 18 by 20 degrees, the angle formed by the straight line connecting the knee P3 and the ankle Q3 of the subject H and the side 18L of the irradiation field 18 may be adjusted to be 0 degrees.

Figure 15:
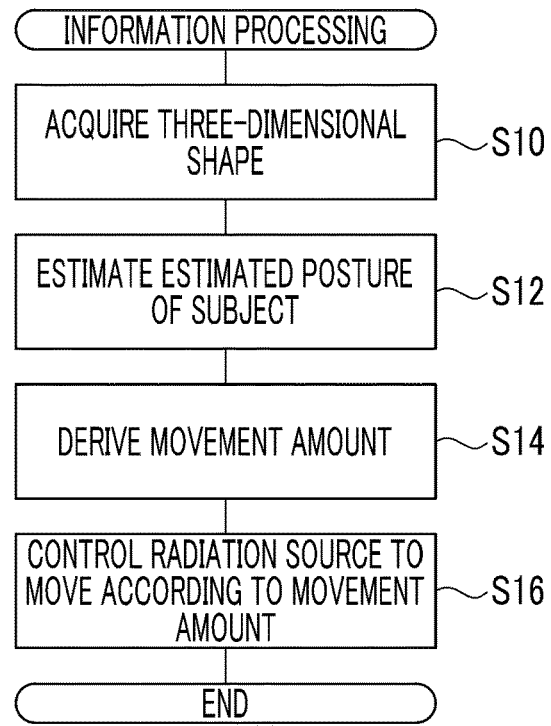
FIG. 15 is a flowchart illustrating an example of information processing.

Next, an action of the console 50 according to the present embodiment will be explained with reference to FIG. 15. In the console 50, the CPU 51 executes the information processing program 57 to execute information processing illustrated in FIG. 15. The information processing is executed, for example, in a case in which the user gives an instruction to start execution via the operating unit 55.

In step S10, the acquisition unit 60 acquires the three-dimensional shape of the subject H measured by the distance-measuring sensor 28 of the imaging apparatus 10. In step S12, the estimation unit 62 estimates a posture taken by the subject H (the estimated posture) based on the three-dimensional shape of the subject H acquired in step S10.

In step S14, the derivation unit 64 derives a movement amount of the radiation source 13 that irradiates the subject H with the radiation R, based on a difference between a predetermined reference posture and an estimated posture estimated in step S12 for the posture of the subject H. In step S16, the controller 66 controls the radiation source 13 to move according to the movement amount derived in step S14 (that is, gives an instruction to the control device 24 of the imaging apparatus 10). In a case in which step S16 ends, the present information processing is ended.

As explained above, the console 50 according to an aspect of the present disclosure comprises at least one processor, in which the processor is configured to acquire a three-dimensional shape of the subject H, derive a movement amount of the radiation source 13 that irradiates the subject H with the radiation R based on a difference between a predetermined reference posture and an estimated posture estimated based on the three-dimensional shape for a posture of the subject H in a case of capturing a radiation image of the subject H, and control the radiation source 13 to move according to the movement amount.

That is, with the console 50 according to the present embodiment, even in a case in which the subject H does not take a predetermined reference posture, the posture taken by the subject H can be estimated based on the three-dimensional shape. In addition, according to the estimated posture that is estimated to be taken by the subject H, it is possible to control the movement of the radiation source 13 to a position where the imaging part can be appropriately imaged. Therefore, a radiation image can be appropriately captured.

In the above-described embodiment, an aspect in which the imaging table 16 is a decubitus imaging table has been explained, but the present disclosure is not limited thereto. The technology of the present disclosure can be applied to, for example, an upright imaging table for imaging the subject H in an upright posture, a sitting imaging table for imaging the subject H in a sitting posture, and the like.

In addition, in the above-described embodiments, for example, as hardware structures of processing units that execute various types of processing, such as the acquisition unit 60, the estimation unit 62, the derivation unit 64, and the controller 66, various processors illustrated below can be used. The above-described various processors include a programmable logic device (PLD) that is a processor of which the circuit configuration can be changed after manufacture, such as a field programmable gate array (FPGA), a dedicated electrical circuit that is a processor having circuit configuration dedicatedly designed to perform specific processing, such as an application specific integrated circuit (ASIC), and the like, in addition to the CPU that is a general-purpose processor functioning as various processing units by executing software (program) as described above.

One processing unit may be formed of one of these various processors, or may be formed of a combination of two or more processors of the same type or different types (for example, a combination of a plurality of FPGAs or a combination of a CPU and an FPGA). In addition, a plurality of processing units may be formed of one processor.

As an example in which a plurality of processing units are formed of one processor, first, there is an aspect in which one processor is formed of a combination of one or more CPUs and software as typified by a computer, such as a client or a server, and functions as a plurality of processing units. Second, there is a form in which, as typified by a system on chip (SoC) and the like, a processor that implements functions of the entire system including the plurality of processing units with one integrated circuit (IC) chip is used. In this way, various processing units are formed using one or more of the above-described various processors as hardware structures.

Furthermore, more specifically, electrical circuitry in which circuit elements, such as semiconductor elements, are combined can be used as the hardware structures of these various processors.

In addition, in the above-described embodiment, an aspect in which the information processing program 57 in the console 50 is pre-stored in the storage unit 52 has been explained, the present disclosure is not limited thereto. The information processing program 57 may be provided in a form in which the information processing program 57 is recorded in recording mediums, such as a compact disc read only memory (CD-ROM), a digital versatile disc read only memory (DVD-ROM), and a universal serial bus (USB) memory. In addition, the information processing program 57 may be downloaded from an external device through a network. Furthermore, the technology of the present disclosure extends to a storage medium for non-temporarily storing the program, in addition to the program.

The technology of the present disclosure can be appropriately combined with the above-described embodiment and examples. The description contents and the illustrated contents above are the detailed explanations of the parts according to the technology of the present disclosure, and are merely examples of the technology of the present disclosure. For example, the above explanations related to configurations, functions, actions, and effects are explanations related to examples of configurations, functions, actions, and effects of the parts according to the technology of the present disclosure. Therefore, it is needless to say that unnecessary parts may be deleted, or new elements may be added or replaced with respect to the description contents and illustrated contents above, within a scope not departing from the spirit of the technology of the present disclosure.

What is claimed is:

1. An information processing apparatus comprising at least one processor, wherein the processor is configured to:
acquire a three-dimensional shape of a subject;
receive a designation of an imaging method;
derive a movement amount of a radiation source that irradiates the subject with radiation based on a difference between a reference posture corresponding to the designated imaging method and an estimated posture of the subject in the case of capturing a radiation image of the subject, the estimated posture being based on the three-dimensional shape; and
control the radiation source to move according to the movement amount; and
wherein the reference posture is predetermined for each imaging method according to an imaging part.

2. The information processing apparatus according to claim 1, wherein the processor is configured to derive a rotation amount of the radiation source about at least one axis as the movement amount.

3. The information processing apparatus according to claim 1, wherein the processor is configured to derive a translation amount of the radiation source in at least one direction as the movement amount.

4. The information processing apparatus according to claim 1, wherein the processor is configured to derive a rotation amount of the radiation source about at least one axis and a translation amount of the radiation source in at least one direction, as the movement amount.

5. The information processing apparatus according to claim 1, wherein the processor is configured to perform a notification in a case in which the derived movement amount exceeds a predetermined threshold value.

6. The information processing apparatus according to claim 1, wherein the processor is configured to:
specify a joint point of the subject based on the three-dimensional shape; and
estimate the estimated posture using the joint point.

7. The information processing apparatus according to claim 1, wherein in a case in which the imaging method is a Stryker method, the reference posture and the estimated posture are determined by an angle formed by a straight line connecting an elbow and a shoulder of the subject and a detection surface of the radiation.

8. The information processing apparatus according to claim 1, wherein in a case in which the imaging method is a lateral radiography of the knee joint, the reference posture and the estimated posture are determined by an angle formed by a straight line connecting a knee and an ankle of the subject and a detection surface of the radiation.

9. The information processing apparatus according to claim 1, wherein in a case in which the imaging method is an Anthonsen view, the reference posture and the estimated posture are determined by
an angle formed by a straight line connecting a heel and a toe of the subject in a sagittal plane and a detection surface of the radiation, an angle formed by a straight line connecting the heel and the toe of the subject in a transverse plane and the detection surface of the radiation, and
an angle formed by a straight line connecting a knee and an ankle of the subject and a side of an irradiation field substantially parallel to a craniocaudal direction of the subject.

10. The information processing apparatus according to claim 1, wherein the processor is configured to acquire the three-dimensional shape measured by a distance-measuring sensor using laser light with 64 rows or more and 512 rows or less.

11. The information processing apparatus according to claim 1, wherein the processor is configured to acquire the three-dimensional shape measured by a time of flight (TOF) camera.

12. The information processing apparatus according to claim 1, wherein the processor is configured to acquire the three-dimensional shape measured by a stereo camera.

13. The information processing apparatus according to claim 5, wherein:
a plurality of threshold values are provided stepwise as the threshold value, and
the processor is configured to:
determine a classification by comparing the derived movement amount with the plurality of threshold values; and
notify of contents according to the classification.

14. The information processing apparatus according to claim 5, wherein the processor is configured to notify whether or not the movement amount is within a predetermined standard range.

15. The information processing apparatus according to claim 5, wherein the processor is configured to notify that it is incapable of capturing the radiation image appropriately.

16. An information processing method comprising:
acquiring a three-dimensional shape of a subject;
receiving a designation of an imaging method;
deriving a movement amount of a radiation source that irradiates the subject with radiation based on a difference between a reference posture corresponding to the designated imaging method and an estimated posture of the subject in the case of capturing a radiation image of the subject, the estimated posture being based on the three-dimensional shape; and
controlling the radiation source to move according to the movement amount; and
wherein the reference posture is predetermined for each imaging method according to an imaging part.

17. A non-transitory computer-readable storage medium storing an information processing program for causing a computer to execute a process comprising:
acquiring a three-dimensional shape of a subject;
receiving a designation of an imaging method;
deriving a movement amount of a radiation source that irradiates the subject with radiation based on a difference between a reference posture corresponding to the designated imaging method and an estimated posture of the subject in the case of capturing a radiation image of the subject, the estimated posture being based on the three-dimensional shape; and
controlling the radiation source to move according to the movement amount; and
wherein the reference posture is predetermined for each imaging method according to an imaging part.

* * * * *